United States Patent [19]
Cohen et al.

[11] Patent Number: 5,840,962
[45] Date of Patent: Nov. 24, 1998

[54] PROCESS FOR PREPARING ESTERS FROM ALCOHOLS AND KETENES

[75] Inventors: Michel Cohen, Naucalpan; Mikhail Khramov, San Luis Potosi, both of Mexico

[73] Assignee: Industrias Monfel S.A. De C.V., Edo De Mexico, Mexico

[21] Appl. No.: 390,070

[22] Filed: Feb. 17, 1995

[51] Int. Cl.[6] ................................................. C07C 67/00
[52] U.S. Cl. .......................................................... 560/239
[58] Field of Search ............................................. 560/239

[56] References Cited

U.S. PATENT DOCUMENTS

| | | | |
|---|---|---|---|
| 2,018,759 | 10/1935 | Frolich et al. | 260/106 |
| 3,651,130 | 3/1972 | Marti et al. | 260/483 |
| 3,679,739 | 7/1972 | Schulz et al. | 260/488 F |
| 3,723,509 | 3/1973 | Matthias et al. | 260/488 R |
| 4,007,184 | 2/1977 | Cronin et al. | 260/250 |
| 4,234,718 | 11/1980 | Brown | 536/69 |
| 4,582,292 | 4/1986 | Ishikawa et al. | 560/57 |
| 4,681,947 | 7/1987 | Stoutamire et al. | 544/370 |
| 4,761,494 | 8/1988 | Petty | 558/398 |
| 4,855,455 | 8/1989 | Kupper | 549/88 |
| 4,940,813 | 7/1990 | Corley et al. | 560/103 |
| 5,294,733 | 3/1994 | McCombs | 560/152 |

FOREIGN PATENT DOCUMENTS

| | | |
|---|---|---|
| 697452 | 11/1964 | Canada . |
| 5576843 | 6/1980 | Japan . |
| 9209552 | 6/1992 | WIPO . |

OTHER PUBLICATIONS

Hurd et al., "Ketene and its Dimer", The Jornal of the Amer. Chem. Society, vol. 61, p. 3355, Dec. 1939.

Quadbeck, "Ketenes in ...Org. Chemistry", Angewandte Chemie, vol. 68, No. 11, pp. 361–370, Jun. 1956.

Quadbeck, "Keten in der prap..Chemie", Angewante Chemie, 68 Jahrgang, Nr. 11, pp. 361–370, Nov. 1956.

Eck, "Acetylierungsreaktionen mit Keten", Chemiker Zeitung, 97, Nr. 2, pp. 62–67, Feb. 1973.

Ponomarev et al., "Using Ketene as an acetylating agent", J. Chem, of the USSR, 21, pp. 1143–1147, 1951 no month provided.

"Keten in der praparativen organischen Chemie", Quadbeck, G.,*Angewandte Chemie,* 68 Jahrgang, Nr. 11, 1956, pg. 361–370.

"Acetylierungsreaktionen mit Keten", H. Eck, *Chemiker Zeitung,* 97 (1973), Nr. 2, pp. 62–67.

*Primary Examiner*—Gary Geist
*Assistant Examiner*—Rosalynd Keys
*Attorney, Agent, or Firm*—Speckman Pauley Petersen & Fejer

[57] ABSTRACT

A process for preparing an ester comprising reacting an alcohol with a ketene in an ester solvent in the presence of an acid catalyst, resulting in a high yield of the ester product, with a minimum of byproducts.

28 Claims, 1 Drawing Sheet

PROCESS FOR PREPARING ESTERS FROM ALCOHOLS AND KETENES

BACKGROUND OF THE INVENTION

1. Field of the Invention

This invention relates to a process for preparing esters by reacting a ketene with an alcohol in the presence of an acid catalyst, which results in substantially complete esterification without producing significant undesirable byproducts, even when polyhydroxy alcohols are used as reactants.

2. Description of Prior Art

It is known in the art to react ketenes with alcohols in the presence of sulfuric acid to produce esters. "Acetylierungsreaktionen mit Keten", H. Eck, *Chemiker Zeitung*, 97 (1973), Nr. 2, pg. 62–67, for example, teaches acetylating polyhydroxy alcohols with ketenes in the presence of sulfuric acid. "Keten in der praparativen organischen Chemie", Quadbeck, G., *Angewandte Chemie*, 68 Jahrgang, Nr. 11, 1956, pg. 361–392, teaches esterifying glycerol with ketene in the presence of sulfuric acid, but indicates only a partial acetylation when using such polyhydroxy alcohols. Neither of these references suggest a process for achieving a high esterification of polyhydroxy alcohols.

There are also several patents disclosing the production of esters. For example, U.S. Pat. No. 3,679,739 teaches a process for preparing esters of acetic acid. The esters are prepared by reacting ketenes with alcohols in the presence of a metal sulfide catalyst in an inert solvent. The '739 patent also discloses reacting ketenes with alcohols in the presence of sulfuric acid, but indicates that undesirable resinous byproducts are often produced. U.S. Pat. No. 4,582,924 discloses a process for preparing α-fluoroalkyl carboxylic acid esters by reacting silyl ketene acetal with acetal ketones or acyl halides. U.S. Pat. No. 5,294,733 discloses several processes for the preparation of cyclic diones and cyclic ester intermediates. These processes primarily use aldehydes and carboxylic acids as reactants with various compounds, including ketenes.

U.S. Pat. No. 4,007,184 teaches a process for preparing alkyl esters of quinoxaline-di-N-oxide-2-carboxylic acid.

Processes for preparing optically active esters are disclosed in U.S. Pat. Nos. 4,681,947 and 4,940,813. U.S. Pat. No. 4,681,947 teaches a process for preparing optically active cyanomethyl esters by reacting non-symmetrical ketenes with optically active α-hydroxynitriles in the presence of an optically active amine catalyst. U.S. Pat. No. 4,940,813 discloses a process for preparing optically active carboxylic acids and esters by reacting ketenes with α-hydroxyesters or α-hydroxyester tertiary amides.

Japanese Patent 55-76843 teaches a process for preparing a β-cyclohexylpropionic acid ester from cyclohexanol and an acrylic ester in the presence of an organic peroxide.

None of the above mentioned patents teach a process for preparing esters that results in substantially complete esterification of polyhydroxy alcohols, without producing undesirable byproducts.

SUMMARY OF THE INVENTION

It is an object of this invention to provide a process for preparing esters using monohydroxy, dihydroxy and polyhydroxy primary, secondary, and tertiary alcohols as reactants.

It is another object of this invention to provide a process for preparing esters which provides a high yield of the desired ester, with a low water content, thus minimizing the formation of water-ester and water-ester-alcohol azeotropes which facilitates to a great extent separation of the desired ester by distillation.

It is yet another object of this invention to provide a process for preparing esters in a continuous operation reaction.

These and other objects are achieved by a process for preparing esters, in accordance with one embodiment of this invention, in which an alcohol and a ketene is reacted in the presence of an acid catalyst, in a solvent of the corresponding ester.

In accordance with another embodiment of this invention, the process takes place in a continuous operation in which a continuous supply of an alcohol and a continuous supply of a ketene are reacted in the presence of an acid catalyst in a first vessel, producing a first vessel product comprising the desired ester. The first vessel product is continuously introduced into a second vessel containing the desired ester product. A portion of the first vessel product is continuously removed from the second vessel, and a second portion of the first vessel product is continuously recirculated from the second vessel to the first vessel.

According to one embodiment of this invention, the process is carried out in a solvent which is initially present in the first vessel, or is circulated to the first vessel from the second vessel. The solvent can be the corresponding ester product, or an inert solvent.

BRIEF DESCRIPTION OF THE DRAWINGS

These and other objects and features of this invention will be better understood from the following detailed description taken in conjunction with the drawing wherein.

DESCRIPTION OF PREFERRED EMBODIMENTS

Figure 1:
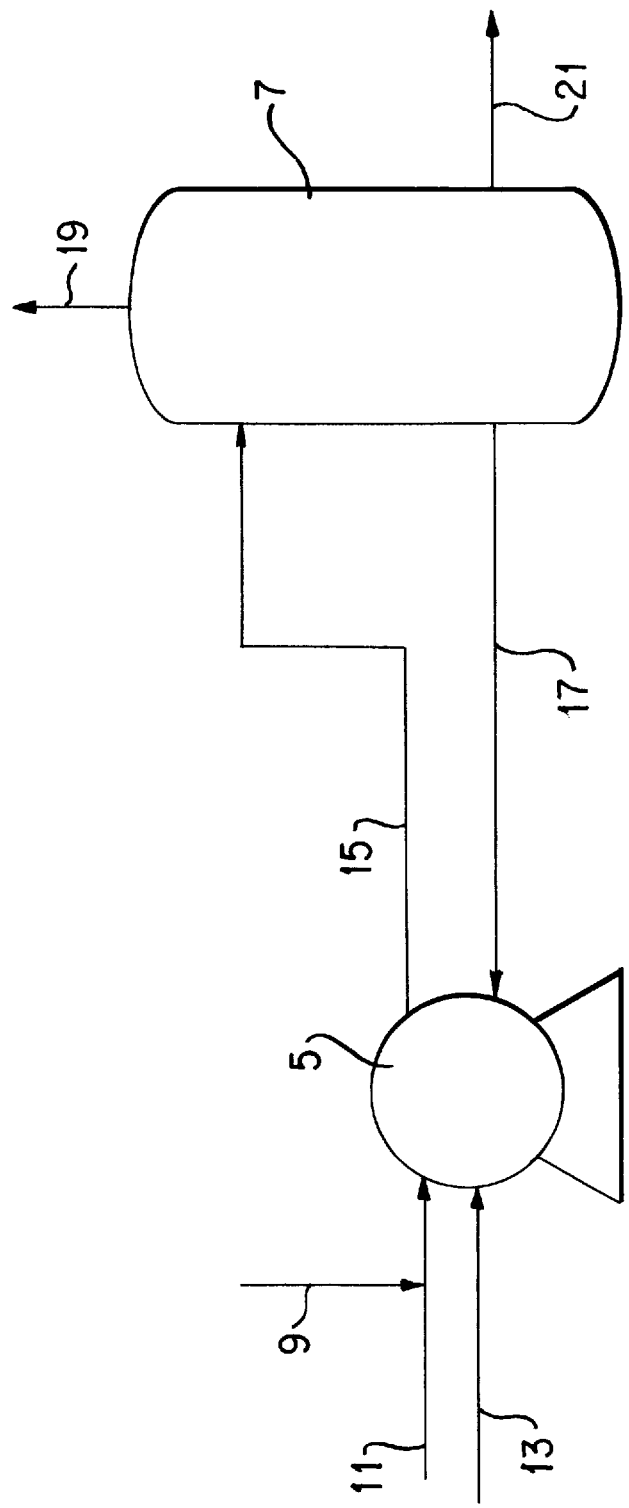
FIG. 1 is a diagram of the flow of reactants and products in a continuous operation according to one preferred embodiment of this invention.

A method for preparing esters by reacting a continuous supply of ketene with a continuous supply of alcohol in a continuous plant operation, according to a preferred embodiment of this invention, can be explained by reference to FIG. 1.

An alcohol is continuously introduced into reactor vessel (first vessel) 5 through line 11. In a preferred embodiment of this invention, an acid catalyst is introduced into the stream of alcohol in line 11 through line 9. It is apparent that the acid catalyst could alternatively be introduced directly into reactor vessel 5. A ketene is continuously introduced into reactor vessel 5 through line 13. The product of the reaction of the ketene and the alcohol is preferably circulated to refrigerator (second vessel) 7 through line 15. Because ketene is highly volatile, in a preferred embodiment of this invention, ventilation is used to remove excess ketene from refrigerator 7 through line 19.

A portion of the product is continuously withdrawn from refrigerator 7 through line 21. Another portion of the product is preferably recirculated back to reactor vessel 5 through line 17, for use as a solvent in the reaction.

The process for preparing esters according to this invention can take place in a solvent of the corresponding ester, in an inert solvent, or without a solvent. According to a preferred embodiment of this invention, refrigerator 7 is first charged with the desired ester product prior to introducing the reactants into reactor vessel 5. According to another preferred embodiment of this invention, reactor vessel 5 is first charged with the desired ester product prior to introducing reactants into reactor vessel 5. If no solvent is first introduced into refrigerator 7 or reactor vessel 5, the product of the reactants can be used as the solvent.

The general formula of ketenes for use in this invention is:

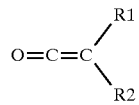

where R1 and R2 are independently selected from the group consisting of hydrogen, alkyl radicals consisting of 1 to 6 carbon atoms, aryl radicals consisting of 6 to 10 carbon atoms, and mixtures thereof. As an example only, the following ketenes are among those that can be used in this invention: ketene, dimethylketene, diethylketene, methylethylketene, and dtiphenylketene. According to a preferred embodiment of this invention, R1 and R2 are hydrogen atoms.

Monohydroxy, dihydroxy, and polyhydroxy primary, secondary, and tertiary alcohols can be used as reactants in this invention, with a good yield provided even when polyhydroxy alcohols are used as reactants. As an example only, the following alcohols are among those that can be used in this invention: methanol, ethanol, n-propanol, isopropanol, butanol, isobutanol, tertbutanol, other monoatomic alcohols, ethyleneglycol, and glycerol. In a preferred embodiment, glycerol or isopropanol is used.

The acid catalyst used in this invention can be selected from the group consisting of sulfuric acid, toluenesulfonic acid, acetosulfuric acid, or other strong acids, and mixtures thereof. The concentration of the acid used, relative to the sum of the weights of the ketene, the alcohol, the solvent and the products of the reaction of the ketene and the alcohol, is in the range of about 0.1% to about 2% by weight. In a preferred embodiment, the concentration is in the range of about 0.3% to about 0.6% by weight.

According to a preferred embodiment of this invention, the pressure inside reactor vessel 5 is in the range of about 0.1 to about 0.8 atmospheres (atm), the most preferred range being about 0.2 to about 0.4 atm. The temperature inside reactor vessel 5 is limited only by the volatility of the reactants. Preferably, the temperature inside refrigerator 7 is kept between about 0° C. and about 100° C., most preferably between about 15° C. and about 40° C.

The process for preparing esters according to this invention provides a high yield of the product ester, even in the case of secondary, tertiary and polyhydroxy alcohols. Furthermore, the ester product contains few byproducts, such as water, which minimizes or eliminates the production and corresponding separation of water azeotropes. Further illustrations of the process according to one embodiment of this invention are provided in the following examples.

EXAMPLE 1

All parts specified are parts by weight.

1. 346 parts of isopropylacetate were charged to refrigerator 7.
2. Ketene was introduced into reactor vessel 5 at the rate of 76 parts per hour.
3. Isopropanol containing 0.7% by weight of sulfuric acid was introduced into reactor vessel 5 at the rate of 110 parts per hour.
4. The recirculation rate from refrigerator 7 to reactor vessel 5 was approximately 3000 parts per hour.
5. The circulation rate from reactor vessel 5 to refrigerator 7 was approximately 3000 parts per hour.
6. The product was withdrawn from refrigerator 7 at a rate wherein the volume of the products in refrigerator 7 remained constant.

After several hours of continuous operation the composition of the products from refrigerator 7 reached a steady state condition. The following table indicates the composition of the solution in the steady state condition withdrawn from refrigerator 7, all numbers being a percentage of weight.

| | |
|---|---|
| isopropylacetate | 82.25 |
| isopropanol | 12.07 |
| acetic acid | 4.90 |
| acetic anhydride | 0.045 |
| water | 0.57 |

EXAMPLE 2

All parts specified are parts by weight.

1. 300 parts of triacetin were charged to refrigerator 7.
2. Ketene was introduced into reactor vessel 5 at the rate of 76 parts per hour.
3. Glycerol containing 1.1% by weight of sulfuric acid was introduced into reactor vessel 5 at the rate of 50 parts per hour.
4. The recirculation rate from refrigerator 7 to reactor vessel 5 was approximately 3000 parts per hour.
5. The circulation rate from reactor vessel 5 to refrigerator 7 was approximately 3000 parts per hour.
6. The product was withdrawn from refrigerator 7 at a rate wherein the volume of the products remained constant.

After several hours of continuous operation the composition of the products from refrigerator 7 reached a steady state condition. The following table indicates the composition of the solution in the steady state condition withdrawn from refrigerator 7, all numbers being a percentage of weight.

| | |
|---|---|
| triacetin | 81.59 |
| diacetins | 0.94 |
| monoacetins | 0 |
| glycerol | 0 |
| acetic acid | 16.81 |
| acetic anhydride | 0.53 |

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A process for preparing an ester comprising the steps of reacting a continuous supply of a ketene having the formula

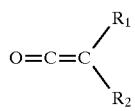

where $R_1$ and $R_2$ are independently selected from the group consisting of hydrogen and organic radicals; with a continuous supply of an alcohol in a solvent comprising said ester in the presence of an acid catalyst in a first vessel, forming a first vessel product comprising said ester;

introducing said first vessel product continuously into a second vessel;

continuously removing a first portion of said first vessel product from said second vessel; and continuously recirculating a second portion of said first vessel product from said second vessel to said first vessel.

2. A process according to claim 1, wherein excess said ketene is continuously removed from said second vessel.

3. A process according to claim 1, wherein said ketene is of the formula

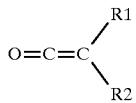

wherein:
R1 and R2 are independently selected from the group consisting of hydrogen, alkyl radicals consisting of 1 to 6 carbon atoms, aryl radicals consisting of 6 to 10 carbon atoms, and mixtures thereof.

4. A process according to claim 3, wherein said ketene is of the formula

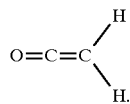

5. A process according to claim 1, wherein said alcohol is selected from the group consisting of monohydroxy, dihydroxy, and polyhydroxy primary, secondary, and tertiary alcohols.

6. A process according to claim 5, wherein said alcohol is selected from the group consisting of glycerol and isopropanol.

7. A process according to claim 1, wherein the pressure in said second vessel is between about 0.1 and about 0.8 atmospheres.

8. A process according to claim 7, wherein the pressure in said second vessel is between about 0.2 and about 0.4 atmospheres.

9. A process according to claim 1, wherein the internal temperature in said second vessel is between about 0° C. and about 100° C.

10. A process according to claim 1, wherein said acid catalyst is selected from the group consisting of sulfuric acid, toluenesulfonic acid, acetosulfuric acid, and mixtures thereof.

11. A process according to claim 1, wherein the concentration of said acid catalyst is between about 0.1 and about 2.0 percent by weight relative to the sum of the weights of said ketene, said alcohol, said solvent and the product of said reaction between said ketene and said alcohol.

12. A process according to claim 11, wherein the concentration of said acid catalyst is between about 0.3 and about 0.6 percent by weight relative to the sum of the weights of said ketene, said alcohol, said solvent and the product of said reaction between said ketene and said alcohol.

13. A process for preparing an ester comprising the steps of:

reacting a continuous supply of an alcohol with a continuous supply of a ketene having the formula

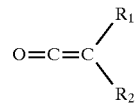

where $R_1$ and $R_2$ are independently selected from the group consisting of hydrogen and organic radicals in a solvent comprising said ester in the presence of an acid catalyst in a first vessel, forming a first vessel product comprising said ester;

introducing said first vessel product continuously into a second vessel containing said ester;

continuously removing a first portion of said first vessel product from said second vessel; and continuously recirculating a second portion of said first vessel product from said second vessel to said first vessel.

14. A process according to claim 13, wherein excess said ketene is continuously removed from said second vessel.

15. A process according to claim 13, wherein said ketene is of the formula

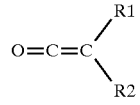

wherein:
R1 and R2 are independently selected from the group consisting of hydrogen, alkyl radicals consisting of 1 to 6 carbon atoms, aryl radicals consisting of 6 to 10 carbon atoms, and mixtures thereof.

16. A process according to claim 13, wherein said ketene is of the formula

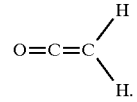

17. A process according to claim 13, wherein said alcohol is selected from the group consisting of monohydroxy, dihydroxy, and polyhydroxy primary, secondary, and tertiary alcohols.

18. A process according to claim 17, wherein said alcohol is selected from the group consisting of glycerol and isopropanol.

19. A process according to claim 13, wherein the pressure in said second vessel is between about 0.1 and about 0.8 atmospheres.

20. A process according to claim 13, wherein the pressure in said second vessel is between about 0.2 and about 0.4 atmospheres.

21. A process according to claim 13, wherein the internal temperature in said second vessel is between about 0° C. and about 100° C.

22. A process according to claim 13, wherein said acid catalyst is selected from the group consisting of sulfuric acid, toluenesulfonic acid, acetosulfuric acid, and mixtures thereof.

23. A process according to claim 13, wherein the concentration of said acid catalyst is between about 0.1 and about 2.0 percent by weight relative to the sum of the weights of said ketene, said alcohol, said solvent and the product of said reaction between said ketene and said alcohol.

24. A process according to claim 13, wherein the concentration of said acid catalyst is between about 0.3 and about 0.6 percent by weight relative to the sum of the weights of said ketene, said alcohol, said solvent and the product of said reaction between said ketene and said alcohol.

25. A process for preparing an ester comprising the steps of:

reacting a continuous supply of an alcohol with a continuous supply of a ketene having the formula

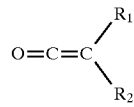

where $R_1$ and $R_2$ are independently selected from the group consisting of hydrogen and organic radicals in the presence of an acid catalyst in a first vessel, forming a first vessel product comprising said ester;

introducing said first vessel product continuously into a second vessel;

continuously removing a first portion of said first vessel product from said second vessel; and continuously recirculating a second portion of said first vessel product from said second vessel to said first vessel.

26. A process according to claim 25, wherein said ketene is of the formula

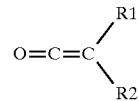

wherein:

R1 and R2 are independently selected from the group consisting of hydrogen, alkyl radicals consisting of 1 to 6 carbon atoms, aryl radicals consisting of 6 to 10 carbon atoms, and mixtures thereof.

27. A process according to claim 25, wherein said alcohol is selected from the group consisting of glycerol and isopropanol.

28. A process according to claim 25, wherein said acid catalyst is selected from the group consisting of sulfuric acid, toluenesulfonic acid, acetosulfuric acid, and mixtures thereof.

* * * * *